(12) United States Patent
Ebi et al.

(10) Patent No.: US 11,660,130 B2
(45) Date of Patent: May 30, 2023

(54) WRIST ARTHRODESIS PLATE AND METHOD USING A WRIST ARTHRODESIS PLATE

(71) Applicant: MEDARTIS HOLDING AG, Basel (CH)

(72) Inventors: Daniel Ebi, Niederdorf (CH); Radek Kebrle, Horejsi Vrchlabi (CZ); Marc Ammann, Pfeffingen (CH); Daniel Kainz, Basel (CH); Simon Martin Schätzle, Gottenheim (DE); Thomas Tribelhorn, Rünenberg (CH)

(73) Assignee: Medartis Holding AG, Basel (CH)

( * ) Notice: Subject to any disclaimer, the term of this patent is extended or adjusted under 35 U.S.C. 154(b) by 0 days.

(21) Appl. No.: 16/970,734

(22) PCT Filed: Feb. 6, 2019

(86) PCT No.: PCT/EP2019/052899
§ 371 (c)(1),
(2) Date: Aug. 18, 2020

(87) PCT Pub. No.: WO2019/162091
PCT Pub. Date: Aug. 29, 2019

(65) Prior Publication Data
US 2020/0375640 A1 Dec. 3, 2020

(30) Foreign Application Priority Data
Feb. 23, 2018 (EP) ..................................... 18158329

(51) Int. Cl.
*A61B 17/80* (2006.01)
*A61B 17/86* (2006.01)
(Continued)

(52) U.S. Cl.
CPC .......... *A61B 17/8061* (2013.01); *A61B 17/86* (2013.01); *A61F 2/42* (2013.01); *A61B 17/848* (2013.01); *A61F 2310/00023* (2013.01)

(58) Field of Classification Search
CPC ....... A61B 17/80; A61B 17/8061; A61F 2/42; A61F 2002/4264; A61F 2/4261
See application file for complete search history.

(56) References Cited

U.S. PATENT DOCUMENTS 5,853,413 A * 12/1998 Carter ................ A61B 17/8061
606/281
6,221,073 B1 * 4/2001 Weiss ................ A61B 17/8061
606/281
(Continued)

FOREIGN PATENT DOCUMENTS

DE 20 2011 051165 U1 1/2012
EP 2158864 A2 * 3/2010 ......... A61B 17/8057
EP 2158864 A2 3/2010

OTHER PUBLICATIONS

Arthrodesen—System 2.0/2.3, 2.5, Medartis See Spec., p. 1.
(Continued)

*Primary Examiner* — Zade Coley
*Assistant Examiner* — Diana Jones
(74) *Attorney, Agent, or Firm* — Finchh & Maloney PLLC

(57) ABSTRACT

A wrist arthrodesis plate (20) consisting of a distal region (21) and of a proximal region (22) which adjoins the distal region (21) in the direction of a longitudinal axis (A). The plate (20) is of such a shape and size that the distal region (21) of the plate can be fastened to the carpus (1) and a proximal region (22) of the plate can be fastened to the radius (3) by fastening devices, such as screws, which can be inserted into plate holes. A distal end region (29), which comprises a farthest distal location (23) of the plate (20), is (Continued)

of a shape and size that the distal end region (29) can be placed with the farthest distal location (23) exactly, and only, on a carpal bone from the group comprising trapezium (11), trapezoid (10), capitate (9) and hamate (8), without covering any part of the laterally adjacent bones.

18 Claims, 4 Drawing Sheets

(51) Int. Cl.
*A61F 2/42* (2006.01)
*A61B 17/84* (2006.01)

(56) References Cited

U.S. PATENT DOCUMENTS

| | | | |
|---|---|---|---|
| 9,668,793 B2 | 6/2017 | Gaudin | |
| 2002/0032446 A1* | 3/2002 | Orbay | A61B 17/7208 606/286 |
| 2007/0265629 A1* | 11/2007 | Martin | A61B 17/8057 606/60 |
| 2009/0248084 A1 | 10/2009 | Hintermann | |
| 2011/0178556 A1 | 7/2011 | Hansson | |
| 2013/0006246 A1* | 1/2013 | Dodson | A61B 17/8061 606/70 |
| 2013/0165979 A1* | 6/2013 | Greenberg | A61B 17/8061 606/280 |
| 2013/0204307 A1* | 8/2013 | Castaneda | A61B 17/8061 606/297 |
| 2017/0000533 A1 | 1/2017 | Fallin et al. | |

OTHER PUBLICATIONS

European Search Report Corresponding to 18158329.5 dated Aug. 17, 2018.
International Search Report Corresponding to PCT/EP2019/052899 dated Apr. 29, 2019.
Written Opinion Corresponding to PCT/EP2019/052899 dated Apr. 29, 2019.

* cited by examiner

WRIST ARTHRODESIS PLATE AND METHOD USING A WRIST ARTHRODESIS PLATE

This application is a National Stage completion of PCT/EP2019/052899 filed Feb. 6, 2019, which claims priority from European patent application serial no. 18158329.5 filed Feb. 23, 2018.

FIELD OF THE INVENTION

The invention relates to wrist arthrodesis plates and to methods using wrist arthrodesis plates according to the characterizing parts of the independent claims.

BACKGROUND OF THE INVENTION

Wrist arthrodesis (wrist fusion) is generally employed to treat painful end states of the wrist. Such end states may have their origin, for example, in very old fractures of the scaphoid bone (scaphoid pseudarthrosis), in late-stage necrosis of the lunate bone (lunatomalacia), or in a collapse of the carpal bones resulting from earlier tearing of the metacarpal ligaments. In particular, fusion may also be effected in cases of painful arthrosis after radial fractures have healed in a defective position, or in cases of advanced, painful arthrosis of an internal origin. Following wrist arthrodesis, the wrist is free from pain again, but stiffened.

For wrist arthrodesis, U.S. Pat. No. 5,853,413 proposes a plate with which the radius, several carpal bones and a metacarpal bone are fused. Over time, the radius, the carpal bones and the metacarpal bone unite and the wrist is thus fused.

With a plate according to U.S. Pat. No. 5,853,413, the wrist is fused over a relatively large area, as a result of which the freedom of movement of the patient's wrist after fusion is very limited.

In its catalog "Arthrodesen-System 2.0/2.3, 2.5", the supplier Medartis proposes a plate in which several carpal bones are fused with the radius. However, in contrast to U.S. Pat. No. 5,853,413, the plate does not extend to a metacarpal bone.

With the proposed plate, the wrist is overall fused to a much lesser extent than with a plate in accordance with U.S. Pat. No. 5,853,413. However, the freedom of movement of the wrist after fusion is still considerably limited.

SUMMARY OF THE INVENTION

It is therefore an object of the invention to minimize the disadvantages of the known plates and in particular to make available a plate which allows a wrist to be free from pain and yet have the as much freedom of movement as possible. The object is achieved by the features of the independent claims.

A wrist arthrodesis plate consisting of a distal region and of a proximal region is proposed. The proximal region adjoins the distal region in the direction of a longitudinal axis. The plate is of such a shape and size that the distal region of the plate can be fastened to the carpus and a proximal region of the plate can be fastened to the radius with the aid of fastening means, in particular screws, which can be inserted into plate holes. A distal end region, which comprises a distal-most location of the plate, is of such a shape and size that the distal end region can be placed precisely, and only, on one bone from the distal row of carpal bones (i.e. the carpal bones of the group comprising os trapezium, os trapezoideum, os capitatum, and os hamatum), without covering part of the laterally adjacent bones.

A plate according to the invention does therefore not extend to the metacarpal bones. The fact that the distal end region can be placed on precisely one carpal bone from the group comprising os trapezium, os trapezoideum, os capitatum and os hamatum is not to be understood here as meaning that the distal region as a whole does not lie over one or more of the further carpal bones. In particular, a distal region can additionally lie also on one of the os scaphoideum, os lunatum or os triquetrum bones (i.e. the proximal row of the carpal bones) and also be screwed to one of these bones. However, the distal end region does not lie on one of the last-mentioned bones and is also not fastened thereto.

The plate according to the invention can typically be used after removal of the proximal row of carpal bones (proximal row carpectomy). In such a case, the first, proximal row of carpal bones (os scaphoideum, os lunatum and os triquetrum) is removed. In this case, the plate according to the invention is placed on and fastened to precisely just one of the distal carpal bones, in particular the capitate.

With the plate according to the invention, it is then precisely just one of the carpal bones from the group comprising os trapezium, os trapezoideum, os capitatum and os hamatum that is fused to the radius. Thus, despite fusion, the patient can be permitted a relatively large freedom of movement. If no proximal row carpectomy takes place, the fusion can take place with the radius and/or with a carpal bone of the proximal row.

By choosing the shape and size of the distal region in accordance with the invention, it is possible that the plate is placed on and fastened to only one of said bones, in particular the os capitatum, without the plate having to be placed on adjacent bones. Preferably, the distal-most location has a maximum width corresponding approximately to the maximum width of a human capitate.

Adjacent carpal bones from the distal row, typically the os hamatum and os trapezoideum, are not covered by the plate.

The distal region and in particular the distal-most end preferably has a width of 10 mm to 15 mm, preferably 12 mm to 14 mm, particularly preferably approximately 13.5 mm. The width of the distal region is measured, perpendicular to the longitudinal axis, between the two lateral-most locations of the distal region (or their projection parallel to the longitudinal axis). These widths have proven advantageous for obtaining a fusion that is sufficient but that is not limiting. This width is preferably also the largest width of the plate as a whole.

The distal region preferably has a length of 15 mm to 30 mm, preferably 15 mm to 20 mm or 20 mm to 27 mm, particularly preferably 16-18 or 21-24 mm. These lengths permit fusion of the wrist without the plate extending into the metacarpus or extending too far or too little on the patient's radius. Too short a length can lead to inadequate fusion. Too long an extent can have a negative impact on the wearing comfort of the plate.

Depending on the indication, plates of different lengths are conceivable. A shorter plate can be used for treatment after a proximal row carpectomy or for treatment of small patients without proximal row carpectomy; a longer plate can be used to provide treatment while preserving the proximal row of carpal bones, or it can be used following proximal row carpectomy in large patients. Typically, the length of the distal region of the aforementioned shorter plate is in the preferred range of 15 mm to 20 mm in the case of a proximal row carpectomy or a small patient. The length of the distal region of the longer plate is 20 mm to 27 mm in the case of treatment with preservation of the proximal row of bones or when treating large patients after a proximal row carpectomy.

A distal-most plate hole of the proximal region can be at a distance of at most 20 mm to 35 mm, preferably 22 mm to 26 mm or 30 mm to 32 mm, from the distal-most location of the plate. Here, the distance from the distal-most plate hole of the proximal region to the distal-most location of the plate is understood as the length of a direct path from a center of the plate hole to the distal-most location of the plate.

Here as well, the aforementioned shorter and longer distances relate respectively to a treatment involving removal or preservation of the proximal row of bones and in small or large patients.

The plate preferably has an overall length, along the longitudinal axis, in the range of 55 to 85 mm, preferably, depending on the type of treatment, of 59 mm to 62 mm or 65 mm to 68 mm.

This range of length has proven advantageous for achieving sufficient fusion between carpal bones and radius without excessively limiting the freedom of movement.

The proximal region preferably has a length of 35 to 60 mm, preferably 40 mm to 50 mm. However, in the proximal region, the plate can also be designed longer, without adversely affecting its intended function.

Preferably, the plate extends in the longitudinal direction at least in a first surface or with a first tangent along the longitudinal axis and additionally extends in the longitudinal direction in a second surface or second tangent, at an angle to the first surface or first tangent, along the longitudinal axis.

The plate can moreover extend in the longitudinal direction in a third surface at a distance from the first surface and approximately parallel thereto.

This embodiment is preferred particularly in connection with the above-described longer plate for providing treatment while preserving the proximal row of carpal bones.

The second surface or the second tangent preferably has an angle of approximately 45° to the first surface and/or extends by a length of 7.5 mm to 8.5 mm, preferably 8.0 mm. In a preferred embodiment, after the second surface, the plate additionally extends in the proximal direction in the third surface or the third tangent along the longitudinal axis, in particular by a length of 8.0 mm to 9.0 mm, preferably 8.5 mm.

After the second surface or after the third surface, the plate can transition in the proximal direction in a fourth surface or along a fourth tangent into the first surface, wherein the fourth surface or the fourth tangent preferably has an angle of about 35° to the first surface and/or extends by a length of 8.5 mm to 9.5 mm, preferably 9.3 mm. Reference is made here to surfaces. Typically, the surfaces each extend substantially in a plane.

In the case of a short plate for treatment with proximal row carpectomy or in small patients, the transition takes place directly from the second to the fourth plane. In the case of treatment with preservation of the proximal row of bones or when treating large patients, the third plane is located between the second and the fourth plane.

It will be appreciated that the mentioned surfaces do not have to be completely planar. One or more curves are conceivable. For this reason, reference is made above to surfaces or tangents.

Such a profile with several surfaces/tangents along the longitudinal direction permits good adaptation of the plate to the anatomy of the carpal bones. In particular, a slightly rounded saddle shape in the distal region allows the distal region to lie well on the carpus. As an alternative to the saddle shape, it is also conceivable that at least planar portions, which form an angle, are present in the longitudinal direction. However, completely flat plates are also conceivable.

Preferably, the proximal region of the plate has a maximum width of 8 to 20 mm, preferably 9 mm to 15 mm, particularly preferably 13.5 mm. The width is again understood as a distance, measured perpendicular to the longitudinal axis, between the two lateral-most locations of the proximal region (or their projection parallel to the longitudinal axis).

Seen in a top view, the distal region preferably has a maximum of in each case two, preferably precisely two, plate holes alongside each other (i.e. within an angle range of +/−45° with respect to an axis approximately perpendicular to the longitudinal axis A) for fastening the plate to the precisely one carpal bone.

Two plate holes, which lie next to each other seen in a top view, permit secure fastening of the distal end region to a single carpal bone.

The distal end region preferably has a maximum of six, preferably precisely six, plate holes for receiving bone screws for fastening the plate to the carpal bone. Of course, the plate can also have further holes, e.g. for a K wire. The four distal plate holes are intended for the capitate, the two proximal plate holes for the lunate. In the case of a large hand and a proximal row carpectomy, a short plate is used, and up to six screws are screwed into the capitate. In the case of a small hand without proximal row carpectomy, a short plate is used and screwed into the capitate and lunate.

The plate holes can preferably be provided with a blocking contour of a kind known to a person skilled in the art, which allows bone screws to be fastened at a stable angle. Such contours are known, for example, from WO 2004/086990 A1.

Alternatively, it is also possible to have a different number of plate holes, for example three, four or five plate holes, in the distal region.

The proximal region preferably has at least two, preferably three, four, five, six, seven, eight, nine or ten or more plate holes in the form of round or oblong holes for bone screws. Preferably, several round holes and one oblong hole are provided.

In the proximal region too, the plate holes for bone screws can be provided with blocking contours, and/or holes can be provided for K wires.

As a result, the proximal region can be securely fastened to the radius.

It is also conceivable to have more than ten plate holes and/or more than or fewer than one plate hole in the form of an oblong hole in the proximal region.

Preferably, the plate contains titanium or consists of titanium. Titanium(alloys) are biocompatible and resistant and have proven optimal for bone plates.

Other biocompatible materials, such as other metals/metal alloys or plastics, are also conceivable.

The invention moreover relates to a method for wrist fusion using a wrist arthrodesis plate, preferably a plate as described above, wherein a proximal region of the plate is fastened to the radius and/or to a carpal bone of the proximal row, and a distal region is fastened to precisely one of the following carpal bones: os trapezium, os trapezoideum, os capitatum and os hamatum.

Fastening to precisely one carpal bone per row achieves a fusion that is sufficient but that does not cover too large an area.

In particular, the plate is not fastened to a metacarpal bone. Moreover, the plate is not fastened to two laterally adjacent carpal bones, but only to at most two carpal bones lying in the longitudinal direction. The distal region is preferably fastened to the carpal bone or carpal bones with a maximum of six screws. The proximal region is preferably fastened with two to six screws.

BRIEF DESCRIPTION OF THE DRAWINGS

Further aspects of the invention can be gathered from the following figures, schematically showing:

FIG. 3a a side view of a first wrist arthrodesis plate according to the invention, FIG. 3b a plan view of the plate according to FIG. 3a, FIG. 4a a side view of an alternative embodiment of a wrist arthrodesis plate according to the invention, and FIG. 4b a plan view of the plate according to FIG. 4a.

DETAILED DESCRIPTION OF THE PREFERRED EMBODIMENTS

Figure 1:
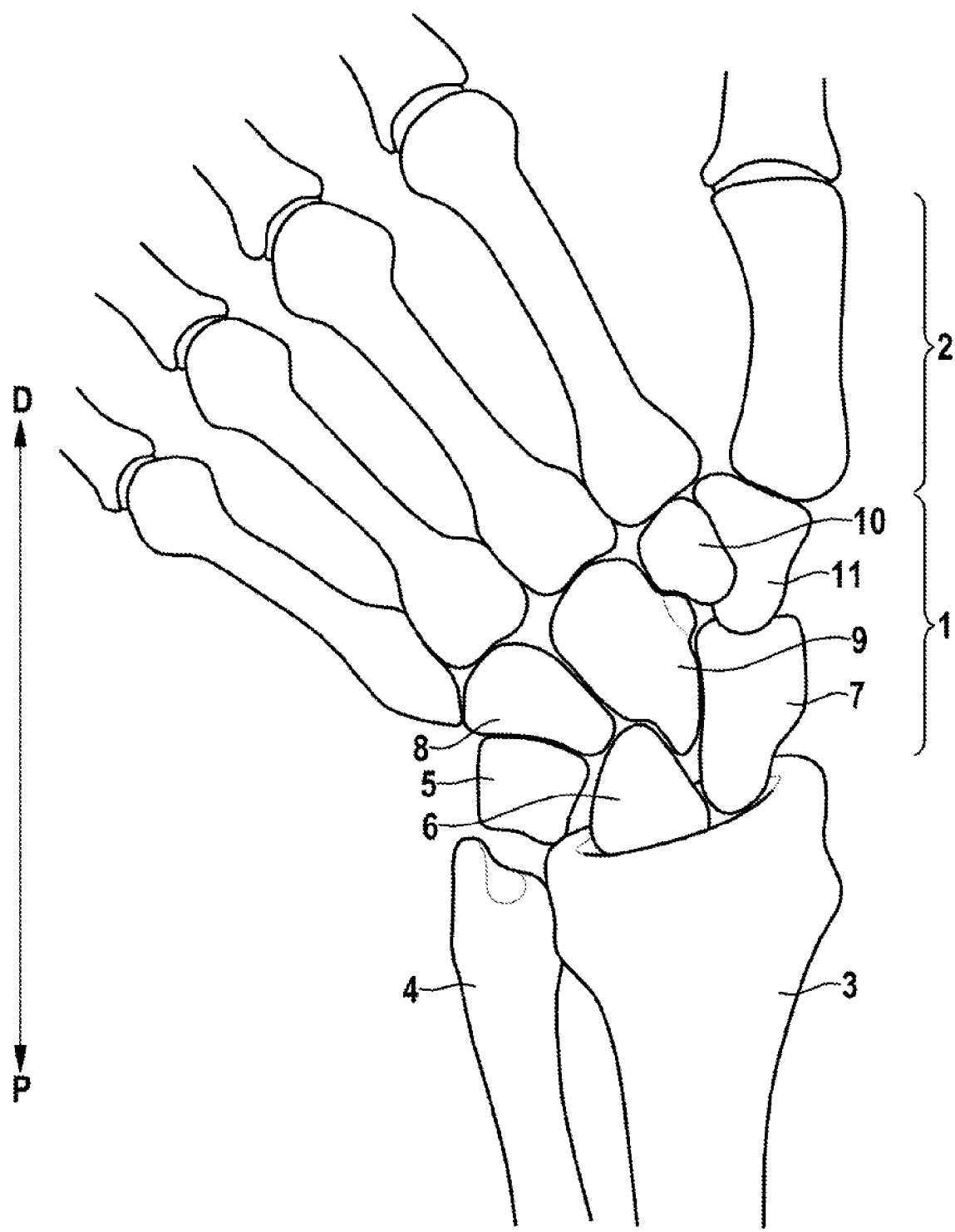
FIG. 1 the anatomy around the wrist.

FIG. 1 shows a schematic representation of the anatomy around the wrist. In the proximal direction P, the carpus 1 adjoins the radius 3 and ulna 4. Distally D from the carpus lies the metacarpus 2. The carpus 1 has the bones os triquetrum 5, os lunatum 6 and os scaphoideum 7. Distally D from the three carpal bones 5, 6, 7 lie the carpal bones os hamatum 8, os capitatum 9, os trapezoideum 10 and os trapezium 11. A distal end region 29 with the distal-most location 23 of the wrist arthrodesis plate 20 according to the invention (see FIG. 2) can be placed on a single one of the four carpal bones os hamatum 8, os capitatum 9, os trapezoideum 10 and os trapezium 11. The bone plate does not extend to the metacarpus 2. Between the proximal region 22 and the distal locations 23, the plate can lie over or on one of the further bones, i.e. os triquetrum 5, os lunatum 6 or os scaphoideum 7, but without being fastened thereto.

Figure 2:
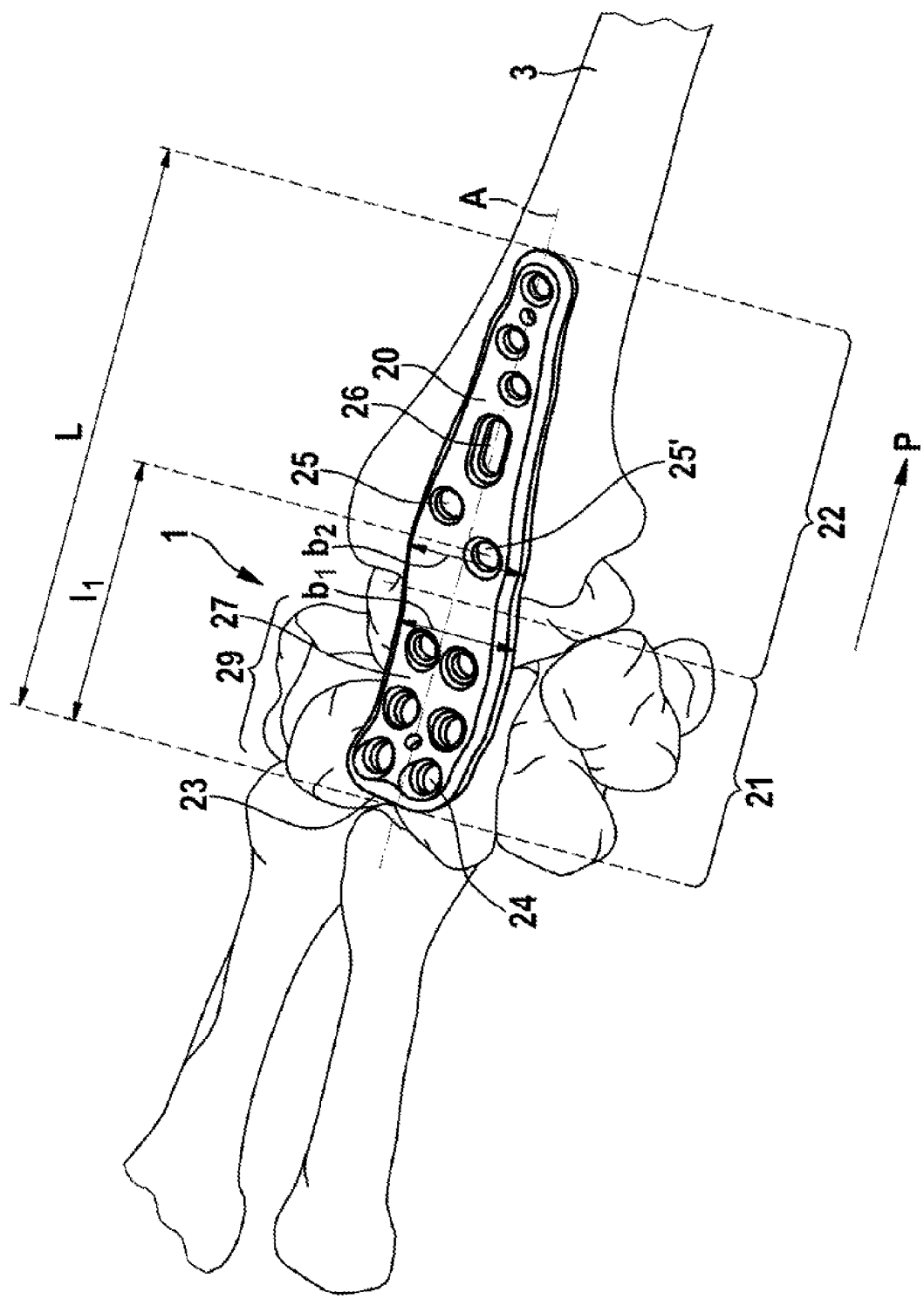
FIG. 2 a wrist arthrodesis plate according to the invention.

FIG. 2 shows a bone plate 20 according to the invention in the intended position of use. The plate 20 is produced from pure titanium or a titanium alloy and has a longitudinal axis A. Along the longitudinal axis A, the plate has a length L of about 55 mm to 85 mm (see also FIGS. 3a/3b and 4a/4b).

The plate 20 is composed of a distal region 21 and of a proximal region 22, which adjoins the latter in the proximal direction P. Depending on the nature of the treatment, the distal region 21 has a length of 16 mm to 28 mm along the longitudinal axis A. The proximal region 22 has a length of ca. 40 mm to 50 mm along the longitudinal axis A.

The proximal region 22 of the plate 20 lies on the radius 3 and can be fastened thereto. The distal region 21 lies on the carpus 1 and can be fastened thereto. The distal end region 29 has six plate holes 24 (only labeled once, for clarity). With screws (not shown), the distal end region 29 can be fastened via the plate holes 24 to a single carpal bone from the group os hamatum 8, os capitatum 9, os trapezoideum 10 and os trapezium 11 (see FIG. 1), without laterally adjacent bones being covered. The proximal region 22 has a plurality of plate holes, specifically five round holes 25, 25' (only labeled once, for clarity) and an oblong hole 26 for fastening the proximal region with screws (not shown) to the radius 3.

The distal region 21 of the plate therefore extends across the carpus 1. However, the distal end region 29 lies on only one of the carpal bones 8, 9, 10, 11 and is also fastened only to said one carpal bone 8, 9, 10, 11. No region of the plate is fastened to the metacarpus 2 or touches the latter.

The distal region 21 has a saddle-shaped depression 27. On account of the depression 27, the plate 20 extends, at the more distal end of the distal end region 29, at an angle of about 10° with respect to a more proximal region of the distal end region 29. The wearing comfort of the plate 20 is increased by this depression 27.

In the proximal region 22, the plate 20 has its widest location with a width b2 of about 13.5 mm. The distal region has a maximum width b1 of about 13.5 mm as well. The widths b1, b2 are measured on a path, perpendicular to the longitudinal axis, between the lateral-most locations, or their projections on an axis parallel to the longitudinal axis A.

Figure 3A:
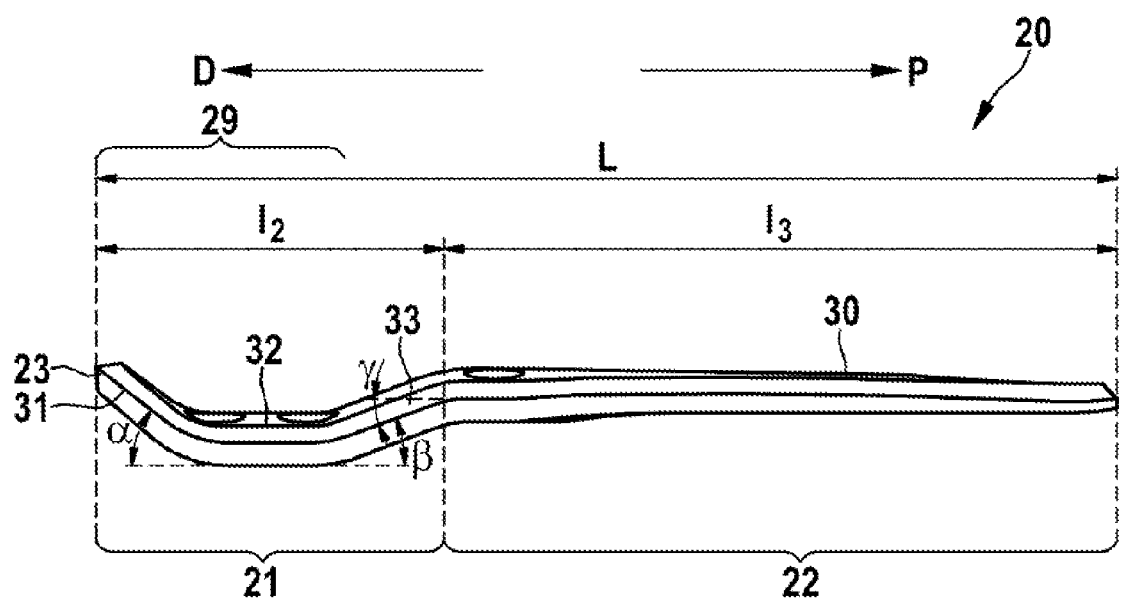
Figure 3B:
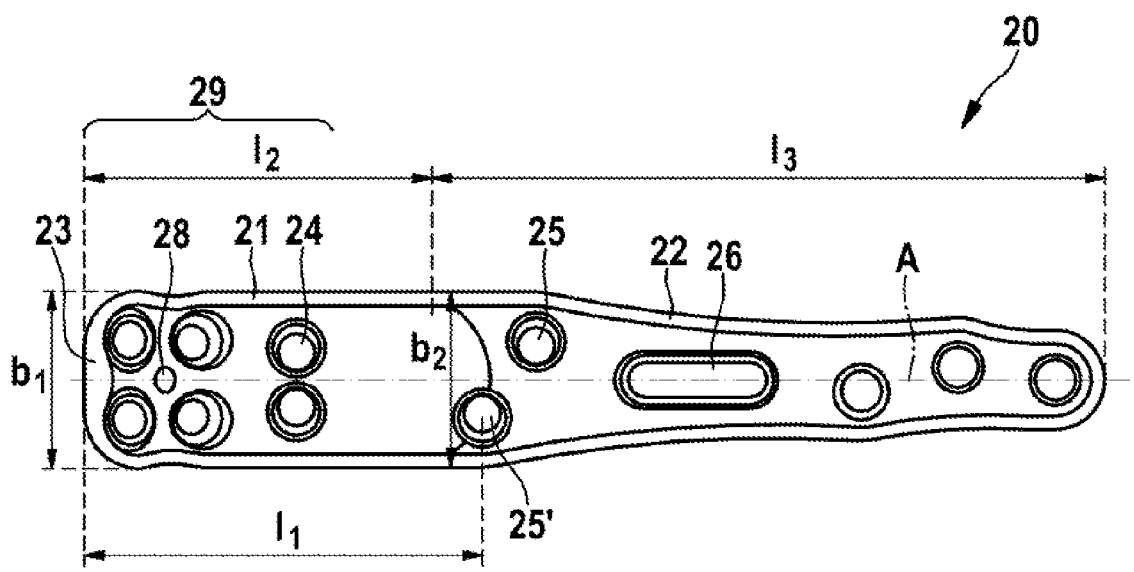

Depending on the nature of the treatment, the distance l1 from the distal-most plate hole 25' of the proximal region 22 to the distal-most end 23 is about 25 mm (see the following description of a short plate in FIGS. 4a and 4b) or 31 mm (see the following description of a long plate in FIGS. 3a and 3b). For reasons of clarity, the length l1 has been indicated outside the plate. The length l1 is measured on a direct path from a center of the distal-most plate hole 25' of the proximal region 22 to the distal-most location 23 of the plate 20.

FIG. 3a shows a first embodiment of a plate 20 according to the invention in a side view. This plate is intended for treatment preserving the proximal row of the carpal bones or for treatment of large patients following a proximal row carpectomy. In the proximal portion 22, with a length l3 of ca. 43 mm, the plate extends in a first surface 30.

Viewed in the proximal direction P from the distal-most end 23, the plate 20 extends in the distal region 21 first in a second surface 31 extending at an angle α with respect to the surface 30. Still in the distal region, the plate then extends in a third surface 32, which is approximately parallel to the first surface 30. By way of a fourth surface 33, the plate transitions from the third surface 32 into the first surface 30. The bend between the fourth surface 33 and the first surface 30 typically also defines the delimitation between the proximal region 22, which can be placed on the radius, and the distal region 21. In the shown embodiment, the length l2 of the distal portion 21 measures 18-22 mm.

In FIG. 3a, the angle α between the second surface 31 and the third surface 32 is about 45°, and the angle β between the third surface 32 and the fourth surface 33 and the angle γ between the fourth surface 33 and the first surface 30 are about 35°.

In the specific example, the first surface 30 and the third surface 32 in FIG. 3a are approximately parallel to each other. However, it is also conceivable to provide a small angle between first surface 30 and third surface 32, for example an angle of up to 10°.

FIG. 3b shows a top view of the plate of FIG. 3a. Identical reference signs denote the same parts. FIG. 3b additionally shows the various holes, in particular plate holes 24 (in the distal region 21) and 25, 25' (in the proximal region 22) for receiving bone screws, a plate hole in the form of an oblong hole 26, and a hole 28 for receiving a K wire. In the proximal region, the plate has a maximum width b2 of about 13.5 mm and tapers in the proximal direction P. In the distal region 21, the plate has a substantially constant width b1, likewise of about 13.5 mm.

Figure 4A:
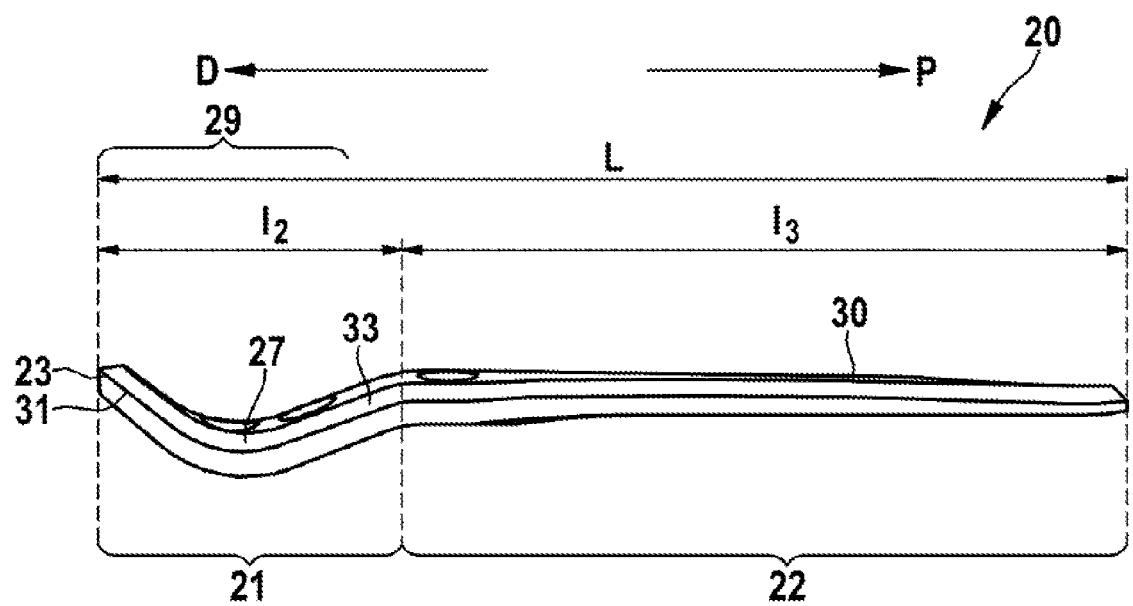
Figure 4B:
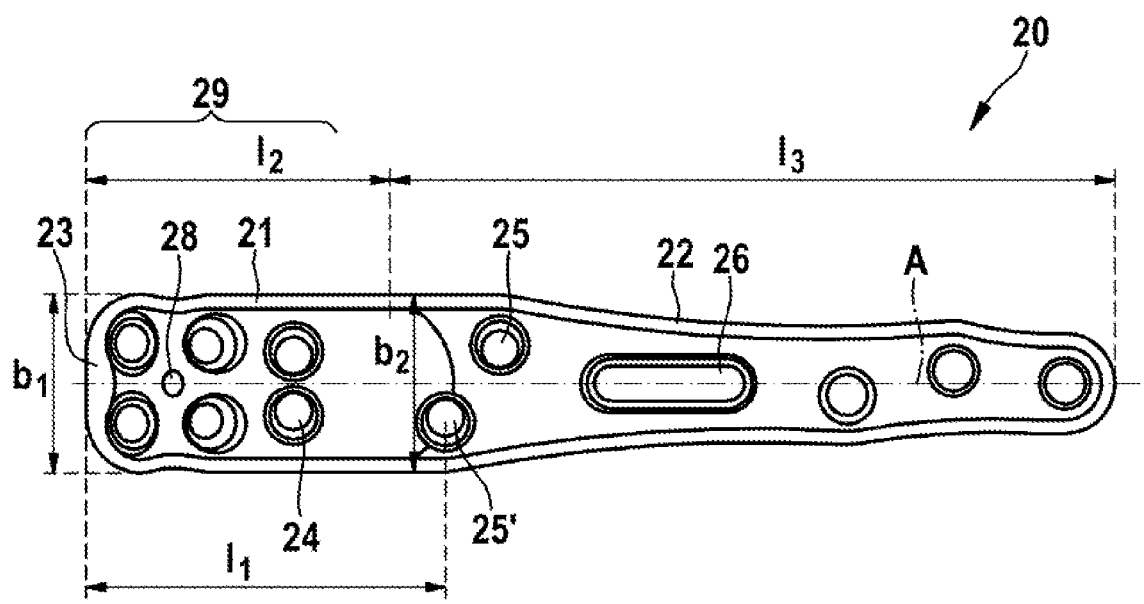

FIGS. 4a and 4b show, analogously to FIGS. 3a and 3b, an alternative embodiment of a plate according to the invention, this plate being suitable for treating a normal-sized hand following a proximal row carpectomy or also for treating a small hand without this intervention. Accordingly, the third surface 32 shown in FIG. 3a is absent: instead, the plate according to the invention shown in FIGS. 4a and 4b transitions directly from the second surface 31 to the fourth surface 33. Accordingly, the length 12 of the distal portion 21 according to FIG. 4a is shorter than in FIG. 3a and typically measures 17 mm. By contrast, the length 13 of the proximal portion 22 is about the same in both embodiments. In the embodiment according to FIG. 4a, the second surface 31 transitions in a gentle radius into the fourth surface 33. The angle position of the second surface 31 and of the third surface 33 with respect to each other and the angle position with respect to the first surface 30 correspond approximately to the angle positions according to the embodiment in FIG. 3a.

The distance of the distal-most plate hole 25' of the proximal part 22 (designated 11 in FIGS. 3b and 4b) from the distal-most end 23 typically measures 25 mm (FIG. 3a) or 17 mm (FIG. 4a).

The lengths of the second, third and fourth surfaces typically measure between 7.5 mm and 10.0 mm. In the specific embodiment, the length of the second surface measures about 8.0 mm, the length of the third surface about 8.7 mm, and the length of the fourth surface about 9.3 mm.

The invention claimed is:

1. A wrist arthrodesis plate for fusion between carpal bones and radius, the carpal bones consisting of a distal row of carpal bones and a proximal row of carpal bones, the distal row of carpal bones being formed by an os trapezium, an os trapezoideum, an os capitatum and an os hamatume and the proximal row of carpal bones being formed by an os scaphoideum, an os lunatum and an os triquetrum,
   said plate defining a longitudinal axis and consisting of a distal region and of a proximal region, wherein the distal region and the proximal region directly and axially adjoin each other in a direction of the longitudinal axis, the plate is fastenable to at most two carpal bones lying in a longitudinal direction and not a metacarpal bone,
   the plate being of such a shape and size that the distal region is fastenable to a carpus and the proximal region is fastenable to a radius with the aid of fastening means, which are inserted into plate holes formed in the distal region and in the proximal region,
   wherein the distal region has (i) a distal end region which comprises a distal-most location of the plate and (ii) a substantially constant width,
   the distal region being of such a shape and size that
   (i) a first area of the distal end region is fastenable to precisely one bone of the distal row of carpal bones, without covering parts of laterally adjacent bones of the distal row of carpal bones,
   (ii) a second area of the distal region is placeable on or over only one bone of the proximal row of carpal bones, and
   (iii) the second area of the distal region is fastenable at most to the bone of the proximal row of carpal bones on or over which it is placeable.

2. The plate as claimed in claim 1, wherein the distal-most location has a maximum width, which corresponds approximately to the maximum width of a human capitate.

3. The plate as claimed in claim 1, wherein the distal region has a width of 10 mm to 15 mm.

4. The plate as claimed in claim 1, wherein the distal region has a length of 15 mm to 30 mm.

5. The plate as claimed in claim 1, wherein a distal-most plate hole of the proximal region is at a distance of at most 20 mm to 35 mm from the distal-most location of the plate.

6. The plate as claimed in claim 1, wherein the plate has a length, along the longitudinal axis, in the range of 55 to 85 mm.

7. The plate as claimed in claim 1, wherein the proximal region has a length of 35 to 60 mm.

8. The plate as claimed in claim 1, wherein the plate extends in the longitudinal direction at least in a first surface or with a first tangent along the longitudinal axis and extends in a second surface or second tangent, at an angle to the first surface or first tangent, along the longitudinal axis.

9. The plate as claimed in claim 8, wherein the angle between the second surface or the second tangent and the first surface or first tangent is about 45°, and/or the second surface extends by a length of 7.5 mm to 8.5 mm.

10. The plate as claimed in claim 9, wherein the plate, after the second surface, extends in a proximal direction in a third surface or a third tangent along the longitudinal axis.

11. The plate as claimed in claim 9, wherein the plate, after the second surface or after the third surface, transitions in the proximal direction in a fourth surface or along a fourth tangent into the first surface.

12. The plate as claimed in claim 1, wherein the plate extends in the longitudinal direction in a third surface at a distance from the first surface and substantially parallel thereto.

13. The plate as claimed in claim 1, wherein the proximal region of the plate has a maximum width of 8 to 20 mm.

14. The plate as claimed in claim 1, wherein the distal region, at an angle range of +/−45° to a perpendicular to the longitudinal axis, has a maximum of four plate holes for fastening the plate to the precisely one bone of the distal row of carpal bones.

15. The plate as claimed in claim 1, wherein the distal end region has a maximum of six plate holes for receiving a bone screw for fastening the plate to the precisely one bone of the distal row of carpal bones.

16. The plate as claimed in claim 1, wherein the plate contains titanium or consists of titanium.

17. A method using a wrist arthrodesis plate according to claim 1 for fusion between carpal bones and radius, the method comprising:
   fastening the proximal region of the plate to one of the radius and a carpal bone of the proximal row, and
   fastening the distal region of the plate to precisely one carpal bone of the distal row of carpal bones.

18. The method as claimed in claim 17, wherein the distal region is fastened to the carpal bone of the distal row of carpal bones with a maximum of four screws.

* * * * *